United States Patent
Bokros et al.

(10) Patent No.: US 6,315,793 B1
(45) Date of Patent: Nov. 13, 2001

(54) PROSTHETIC VENOUS VALVES

(75) Inventors: Jack C. Bokros; Jonathan C. Stupka; Robert B. More, all of Austin, TX (US)

(73) Assignee: Medical Carbon Research Institute, LLC, Austin, TX (US)

(*) Notice: Subject to any disclaimer, the term of this patent is extended or adjusted under 35 U.S.C. 154(b) by 0 days.

(21) Appl. No.: 09/392,234

(22) Filed: Sep. 8, 1999

(51) Int. Cl.$^7$ ........................................... A61F 2/06
(52) U.S. Cl. ............................. 623/1.24; 623/1.1
(58) Field of Search ........................ 623/1.24, 1.16, 623/2.26, 2.35, 2.34; 137/541, 329.03; 251/82

(56) References Cited

U.S. PATENT DOCUMENTS

| | | | |
|---|---|---|---|
| 3,294,116 | 12/1966 | Tremeau | 137/541 |
| 4,015,590 | 4/1977 | Normann | 128/1 |
| 4,086,665 | 5/1978 | Poirier . | |
| 5,272,909 | 12/1993 | Nguyen et al. | 73/37 |
| 5,358,518 | 10/1994 | Camilli | 623/2 |
| 5,397,351 | 3/1995 | Pavenik et al. | 623/11 |
| 5,500,014 | 3/1996 | Quijano et al. | 623/1 |
| 5,601,580 | 2/1997 | Goldberg et al. | 606/159 |
| 5,607,465 | 3/1997 | Camilli | 623/1 |
| 5,697,968 | 12/1997 | Rogers et al. | 623/1 |
| 5,824,061 | 10/1998 | Quijano et al. | 623/2 |

FOREIGN PATENT DOCUMENTS

| | | |
|---|---|---|
| 19619089A1 | 11/1997 | (DE) . |
| 19619089 | * 11/1997 | (DE) ........................... A61F/2/06 |

OTHER PUBLICATIONS

Qui, et al., "Fluid Dynamics of Venous Valve Closure", Annals of Biomed Engineering, vol. 23, pp. 750–759, 1995.
Qui, et al., "A Formula for Venous Valve Performance", BED–vol. 22, Advances in Bioengineering, ASME, pp. 521–524, 1992.

* cited by examiner

Primary Examiner—Corrine McDermott
Assistant Examiner—Thomas Barrett
(74) Attorney, Agent, or Firm—Fitch, Even, Tabin & Flannery

(57) ABSTRACT

A prosthetic venous valve having a two-piece housing which includes upstream and downstream sections. The upstream section contains a circular seat against which an occluder comes in sealing contact when the valve is in its closed position. The downstream housing section is shaped so as to prevent escape of the occluder downstream and to halt the reciprocating motion of the occluder in the open position where there is an open pathway past the occluder. A plurality of fins on the interior of the downstream housing section or on the surface of the occluder assure there is a blood flow path downstream past the occluder in the open position. The two-piece construction allows the housing sections to be axially spaced apart so that blood comes in contact with the interior surface of the patient's vein immediately downstream of the upstream section of the housing. Such arrangement is biologically advantageous and permits momentary deflections of either of the housing sections from its normal coaxial orientation without harm to the valve or disruption of its functioning.

19 Claims, 5 Drawing Sheets

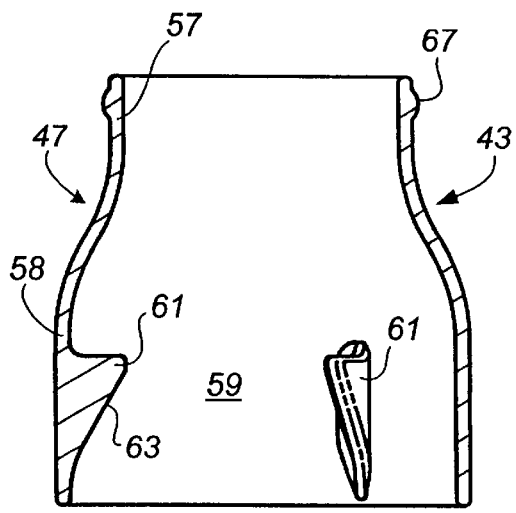
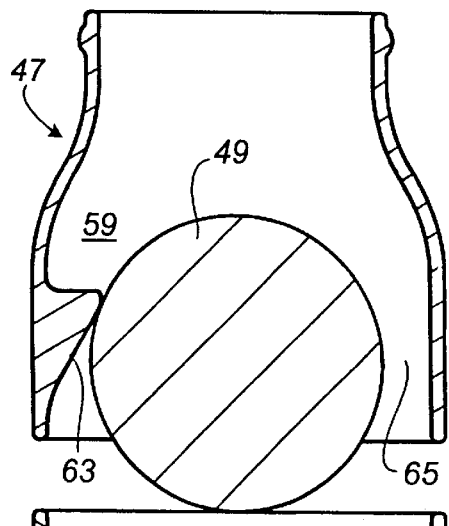
FIGURE 5
FIGURE 6
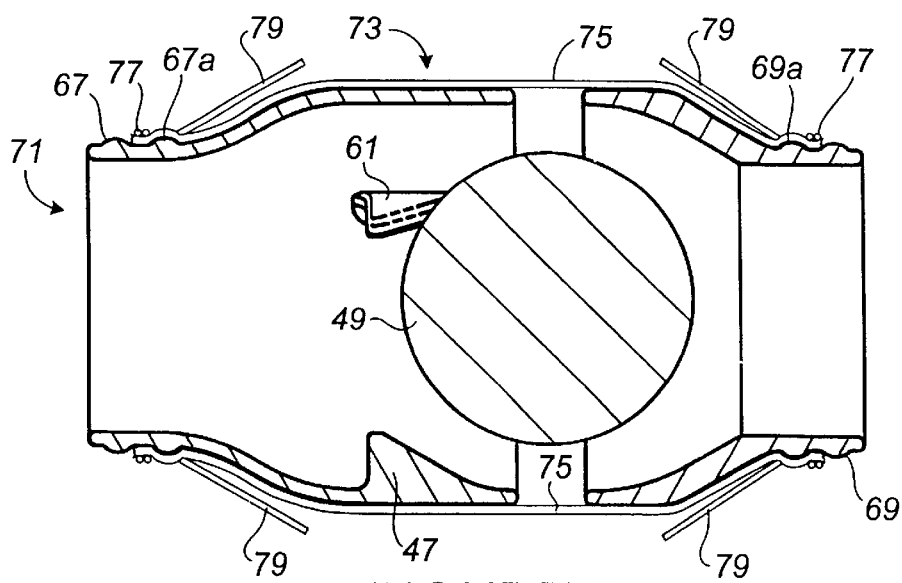
FIGURE 7

PROSTHETIC VENOUS VALVES

FIELD OF THE INVENTION

The present invention relates to prosthetic valves for replacement use in patients and more particularly to replacement venous valves that can take the place of a malfunctioning valve in a blood vessel of a patient.

BACKGROUND OF THE INVENTION

The distribution and transportation of blood between different parts of the body is regulated by many physical factors, and the lack of knowledge with respect to venous flow and the behavior of venous valves has often made current treatment of venous disorders ineffective. In the last decade, a fair amount of attention has been given to difficulties that occur in circulation in humans that result from nonoperative or malfunctioning venous valves. Apparatus and medical procedures have been developed for excising such malfunctioning valves.

Venous valves act to assist the return of venous blood to the heart as part of the physiological pumping system known as the "venous pump" or "muscle pump". Venous valves are one-way valves arranged so that the direction of blood flow can only be towards the heart. Every time the legs are moved, or muscles tensed, a bolus of blood is propelled towards the heart. This bolus, moving towards the heart, opens and crosses a venous valve. Reverse flow is then prevented by the closing action of the venous valve. In the next movement or contraction, the venous blood bolus is lifted through the next venous valve and so forth until it has returned to the heart from the lower extremities via the venous or muscle pump. This venous pump is independent of the contraction of the heart.

Venous return from an extremity of the body is not actually dependent upon properly functioning valves when a patient is in the supine position because the existing pressure gradient to the heart may be sufficient to assure normal return. However, proper functioning of venous valves in the lower extremities can be of critical importance in minimizing pressure build up when the body is not in the supine position. Unfortunately, diagnosis of a problem with one or more venous valves has not been sufficient because there are currently no known commercially available prosthetic valves that can function satisfactorily as a replacement for a malfunctioning native valve.

Some relatively simple, experimental venous valves have been developed, such as those shown in U.S. Pat. Nos. 5,358,518, 5,500,014, and 5,607,465, and one somewhat more complicated venous valve implant is shown in U.S. Pat. No. 5,824,061. Moreover, a double-ball check valve and intraluminal graft is shown in U.S. Pat. No. 5,697,968, and a self-expanding poppet valve that can be inserted through a catheter while confined in a tubular sheath is shown in U.S. Pat. No. 5,397,351.

The potential for thrombosis at replacement venous valves is a very important consideration for, because of its very nature, the valve is always in contact with blood; thus, such must be given the utmost attention. As one alternative, devices have also been designed to simply bypass venous valves by holding them open, such as that shown in U.S. Pat. No. 5,843,171. In addition, devices have been constructed to test the operation of both artificial and natural venous valves, such as that shown in U.S. Pat. No. 5,272,909. However, despite the considerable work that has gone into this area, satisfactory solutions have not yet been achieved; thus, the search for more satisfactory prosthetic venous valves has continued.

SUMMARY OF THE INVENTION

Improved prosthetic venous valves have now been developed which have a two-piece housing arrangement. The two housing pieces are separated from each other but are so associated with the vein of a patient as to confine an occluder or poppet in an operative location. In one preferred embodiment, a generally tubular two-piece housing is made of rigid material and designed to be positioned within the vein in a spaced-apart relationship, separated from each other by a short section of the interior of the vein itself. A first or upstream section of the housing is formed with a seat which is shaped so as to provide a seal when in contact with the occluder or poppet, which has a suitable shape, e.g. that of a sphere; the occluder is confined within the valve housing so it can shift between the interiors of the upstream section and the downstream section of the housing. The downstream section should have an interior surface that cooperates with the occluder so as to prevent the occluder's escape downstream and position it within the interior of the two-piece valve housing in a way to provide an open discharge pathway for blood to flow through the venous valve in response to pumping. Occluders of several different shapes may be used.

The invention also envisions a housing having a more elongated upstream section that confines and generally guides an elongated occluder and that allows a downstream section to be installed exterior of the vein. The invention also envisions the incorporation of a surrounding retainer, such as a wire harness arrangement or a perforated tube or the like that spaces the separate sections of the housing a desired distance apart, which harness arrangement could additionally include detents or splines that would engage the interior surface of the vein and immobilize the prosthetic venous valve at the desired location within the vein.

BRIEF DESCRIPTION OF THE DRAWINGS

FIG. 3 is a plan view of the valve of FIGS. 1 and 2 with the section line 2—2 showing the plane along which FIGS. 1 and 2 are sectioned.

FIGS. 5 and 6 are sectional views, similar to FIGS. 1 and 2, of an alternative embodiment of a prosthetic venous valve embodying various features of the invention.

FIG. 7 is a view similar to FIG. 4 of a slightly modified version of the valve of FIGS. 5 and 6 with the occluder shown in an intermediate position between the closed and fully open position.

FIG. 9A is a perspective view of the valve of FIG. 8 shown in its open position.

DETAILED DESCRIPTION OF THE PREFERRED EMBODIMENTS

Figure 1:
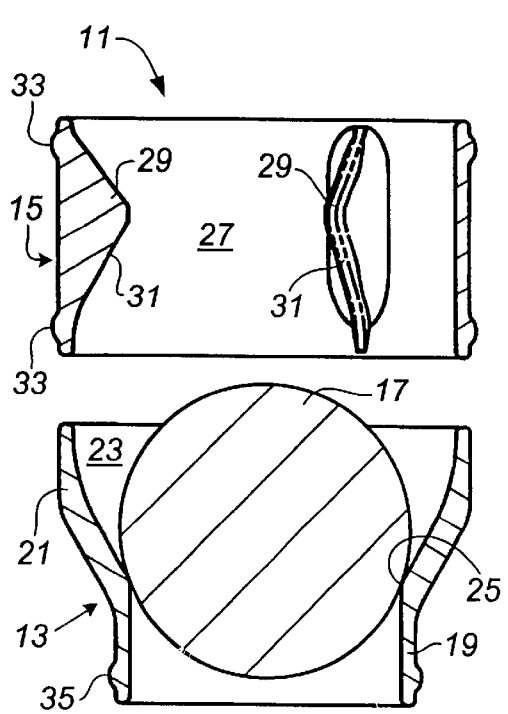
FIG. 1 is a sectional view through a prosthetic venous valve embodying various features of the present invention, showing the ball occluder in closed position in contact with the upstream seat.

Illustrated in FIG. 1 is a prosthetic venous valve 11 which embodies various features of the present invention. The valve includes separate upstream and downstream housing sections 13, 15 and an occluder 17 which is designed to travel back and forth within the interior confines of the separate housing sections.

The upstream section 13 is generally tubular in shape, being of circular cross-section and having an entrance end 19 of reduced diameter relative to a main body portion 21, which provides an interior central region 23 of greater diameter than the occluder 17. The transition surface between the entrance end portion 19 and the sloping interior wall surface of the central region 23 forms a seat 25 for the ball occluder 17. When the occluder 17 is in contact with the seat 25, upstream liquid flow vertically downward (in the orientation shown in FIG. 1) is positively prevented.

Figure 2:
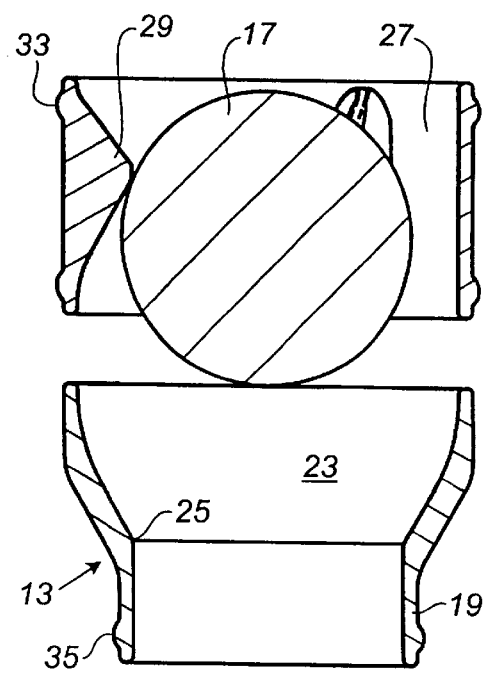
FIG. 2 is a view similar to FIG. 1 showing the ball occluder in open position.
Figure 3:
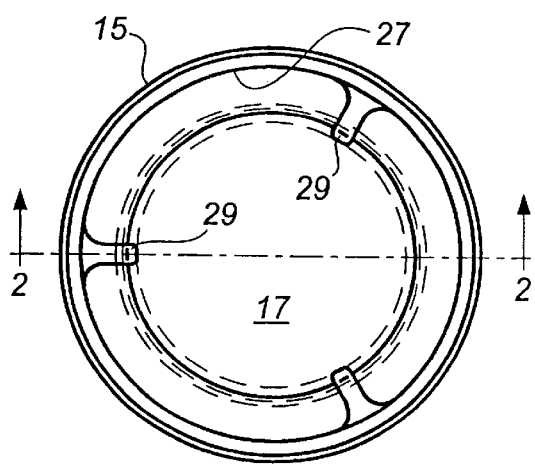

The downstream housing section 15 is also generally tubular in shape having an interior surface 27 which is generally the shape of a right circular cylinder except for one or more, preferably three, radially extending detents 29. The diameter of the interior surface 27 is larger than the diameter of the occluder 17 so that blood can always flow freely through the downstream section 15 regardless of the position of the occluder 17. The detent or detents 29 may generally have the shape of a triangular fin which is thicker at its base than at the tip; they preferably have upstream walls which guide the ball occluder to a central location where it abuts the three detents when there is blood flow in a downstream direction through the valve 11. As best seen in FIG. 3, the detents 29 extend radially into the interior of the central region of the downstream section of the housing to a sufficient extent to block the passage of the occluder 17 therethrough. As best seen in FIG. 2, when the venous valve 11 is in the open position with downstream flow occurring, which in this instance is radially upward through the valve 11, the occluder 17 is centered within the central region by contact with the three detents 29 leaving three large open regions between the fins 29 (which are aligned at 120° intervals) through which blood can freely flow. With less than three detents, the occluder might not be centered but will still provide the desired downstream flow passageway.

Figure 4:
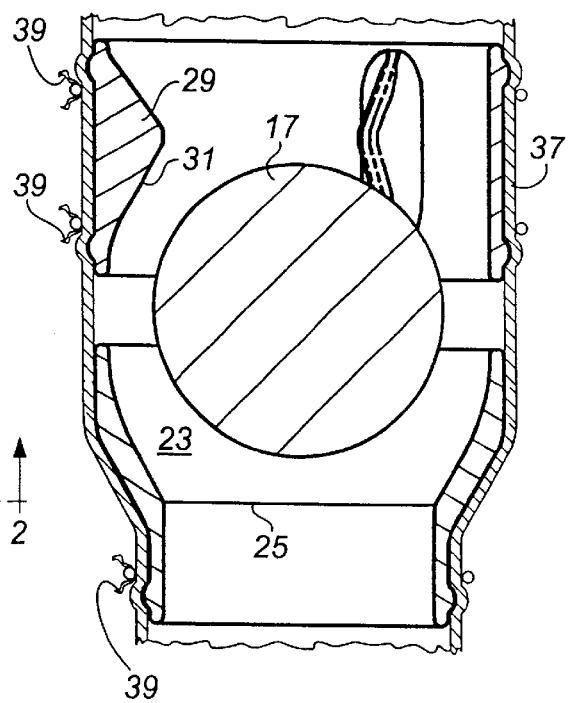
FIG. 4 is a view similar to FIGS. 1 and 2 showing the valve installed in the vein of a patient with the occluder at an intermediate location between the closed and fully open positions, depicted in FIGS. 1 and 2, respectively.

To secure the valve 11 in place within a patient's vein, a pair of circular ridges 33 are provided on the exterior surface of the downstream section of the housing 15, one generally adjacent each end, and a similar circular ridge 35 is provided on the exterior surface of the reduced diameter upstream end 19 of the upstream housing section 13. FIG. 4 depicts the valve 11 in place in the vein of a patient.

To install the valve 11, the surgeon may slit the vein to excise the native valve using a venous valve cutter such as that shown in U.S. Pat. No. 5,601,580. Once the malfunctioning valve has been excised, the prosthetic venous valve 11 can be installed requiring only a minimal slit in the sidewall of the vein because of the two-piece construction. For example, a slit might be made downstream of the defective valve, and after excising it, the upstream section 13 of the housing could first be installed and then secured in place using a surgical tie 39 in the region between the ridge 35 and the outwardly expanding surface of the main body portion 21, as shown in FIG. 4. Thereafter, the downstream section 15 which may carry the ball occluder 17, as generally shown in FIG. 2, would be installed so as to be positioned at the appropriate spaced-apart distance from the upstream section. It is secured in place by two ties 39 positioned inboard of the ridges 33.

The distance between the adjacent central ends of the two housing sections is preferably between about 20 and 35% of the diameter of the spherical occluder 17. This spacing is preferred for a prosthetic valve 11 wherein the diameter of the interior surface 27 is between about 120% and about 140% of the diameter of the occluder; more preferably, the interior diameter of the downstream section is between about 125% and about 135% of the diameter of the occluder. With such a relationship, the two-piece construction has particular advantages. In addition to facilitating manufacture of the venous valve 11, the implanted arrangement reduces the amount of contact between blood and the foreign material from which the housing is constructed by providing a short section of natural vein within the interior of the valve itself, thus reducing the pathway created from foreign material into two shorter sections separated by a section of natural vein. Even more importantly, there is provided a certain flexibility which allows some displacement between the two sections of the housing in a direction transverse to the axis through the valve 11, and this can be an important feature for a venous valve that may be located near the surface of the patient's leg or the like where flexure to coaxial alignment will likely occur during exercise and/or as a result of other contact with objects outside the body. The three converging upstream walls 31 of the fins 29 always center the ball occluder at the axis in the full open position, and the sloping walls of the interior of the central region 23 of the upstream section likewise smoothly guide the ball to the seat 25. It can be seen from FIG. 4 that this relationship of the occluder 17 with each of the housing sections 13, 15 is independent of the other, and thus the valve will continue to operate even if there should be deflection of one of the housing sections in a transverse direction so that both are momentarily no longer coaxial.

The housing sections 13, 15 and the occluder 17 can be made of any suitable non-thrombogenic biocompatible material, e.g. titanium, titanium-nickel alloys, dense molded polymeric materials and the like; however, the preferred materials for construction of the valve housing and the occluder are pyrolytic carbon (pyrocarbon) and pyrocarbon-coated graphite. Most preferred is material made from a graphite substrate coated with On-X™ pyrocarbon, which is available from Medical Carbon Research Institute, LLC, of Austin, Tex. and which is described in detail in U.S. Pat. No. 5,514,410, issued May 7, 1996. Because there will not be a large pressure gradient driving the flow of blood through a venous valve when the body is in a supine position, it may be desirable to utilize an occluder 17 which has a density close to the density of human blood. Such an occluder will tend to incur more movement during times of low pressure gradients, minimizing the potential for stasis and possible thrombus formation.

Depicted in FIGS. 5 and 6 is an alternative embodiment of a venous valve 43 embodying various features of the invention which it will be recognized as having similarity to the venous valve 11. The valve 43 has an upstream housing section 45, a downstream housing section 47 and a ball occluder 49. The upstream housing section 45 has essentially the same construction as the section 13 depicted in FIG. 1. It includes an entrance portion 51 of reduced diameter and a main body portion 53 wherein there is a seat 55 for the ball occluder 49.

The downstream housing section 47 has an axial length about twice that of the section 15 with a downstream exit portion 57 of reduced diameter. The downstream housing section functions the same as the downstream section 15, having a central region 58 with an interior surface 59 from which three triangular fins 61 having diagonally oriented guide edges 63 protrude radially inward and provide three open flow passageways 65. The extended downstream end 57 of the housing section 47 facilitates securing the venous valve within the vein, and its exterior surface contains a similar circular ridge 67. A similar circular ridge 69 is provided on the exterior surface of the upstream housing section 45. The axially extended downstream housing section 47 facilitates smooth interconnection with the vein and smooth flow downstream from the prosthetic valve 43.

Depicted in FIG. 7 is a valve 71 which is the same as the valve 43 except for the inclusion of two additional circular ridges 67a and 69a, and accordingly the other elements are referred to using the same reference numerals as in the valve 43. The valve 71 incorporates a surrounding retainer which may be in the form of a wire cage 73 that includes a plurality of longitudinally extending strands 75 of radioopaque wire, which extend from end to end, and a plurality of coils 77 at each end, where the wire is wrapped about the reduced diameter entrance and exit ends of the valve in the regions respectively between the circular ridges 67 and 67a and 69 and 69a. Thus, these strands 75 bridge the center gap between the two spaced-apart housing sections 45, 47, uniting the two spaced-apart sections. Other equivalent surrounding retainer structures may alternatively be used.

The valve 71, with the two spaced-apart housing sections 45, 47 appropriately assembled and spaced apart from each other within the wire cage 73 provides a device which, for example, might be installed through a thin-walled catheter inserted into the vein from which the malfunctioning valve has been excised. As an option, the wire cage 73 may be formed with a plurality of barbs 79 of spring-like character that can be positioned to lie against the exterior of the housing but, upon release, will extend outwardly to the orientation shown in FIG. 7 and engage the interior surface of the vein. As shown therein, barbs 79 associated with the upstream section 45 extend diagonally downstream and vice-versa. Accordingly, the valve 71 with the illustrated wire cage 73 would reasonably be installed within a thin sheath when transported, as for example within a catheter, to the desired location in the vein of the patient. When the valve is correctly positioned, the sheath is withdrawn, and the barbs 79 spring radially outward and affix the valve 71 within the vein. The wire and the barbs or other surrounding retainer can be made of tantalum, titanium or an appropriate alloy thereof which is biocompatible and preferably radioopaque so that it will be prominently displayed on any x-ray radiograph. Generally, the structure, e.g. wire, should have sufficient thickness or size to resist inadvertent bending so as to maintain desired spacing invivo within a patient.

Figure 8:
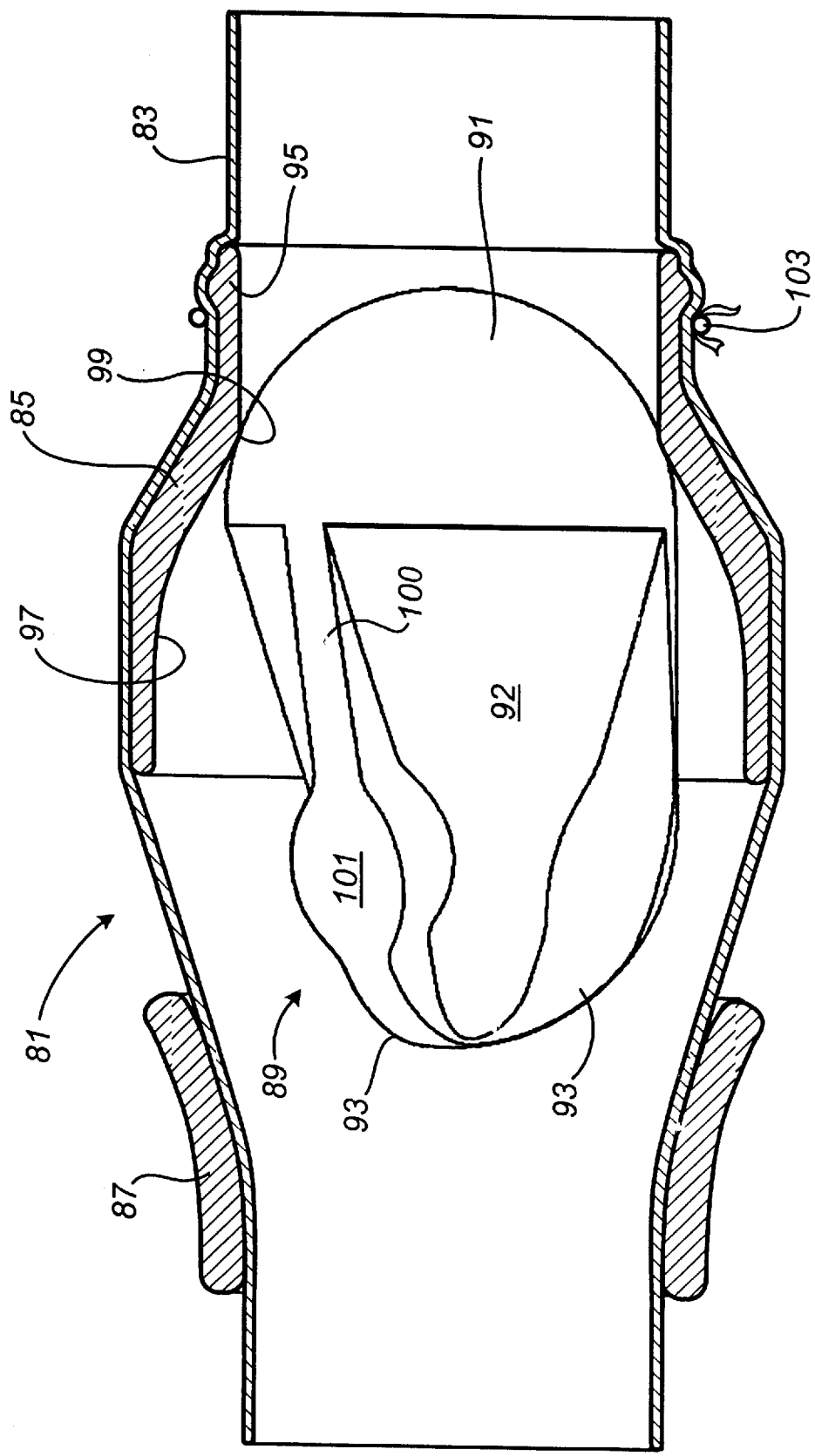
FIG. 8 is a view similar to FIG. 4 of another prosthetic venous valve embodying various features of the invention, with the body shown in cross-section and the occluder shown in elevation in closed position.

Illustrated in FIG. 8 is another alternative two-piece venous valve 81 which is shown in place in the vein 83 of a patient. The valve 81 differs from those previously described in that its upstream housing section 85 is elongated and its downstream housing section is disposed exterior, rather than interior, of the vein 83. The elongated upstream section 85 complements an elongated occluder 89, and the downstream section is in the form of a split collar 87. The elongated occluder 89 has a generally hemi-spheroidal upstream end 91 and is smoothly reduced in cross-sectional area along its length toward the downstream end; it has a length at least about twice that of its diameter. Its contour is such to create three valleys 92 located between three generally axially extending fins 93, that are regularly spaced apart from one another at about 120° intervals. Although two or four or more fins might be used, three are preferred.

Figure 9:
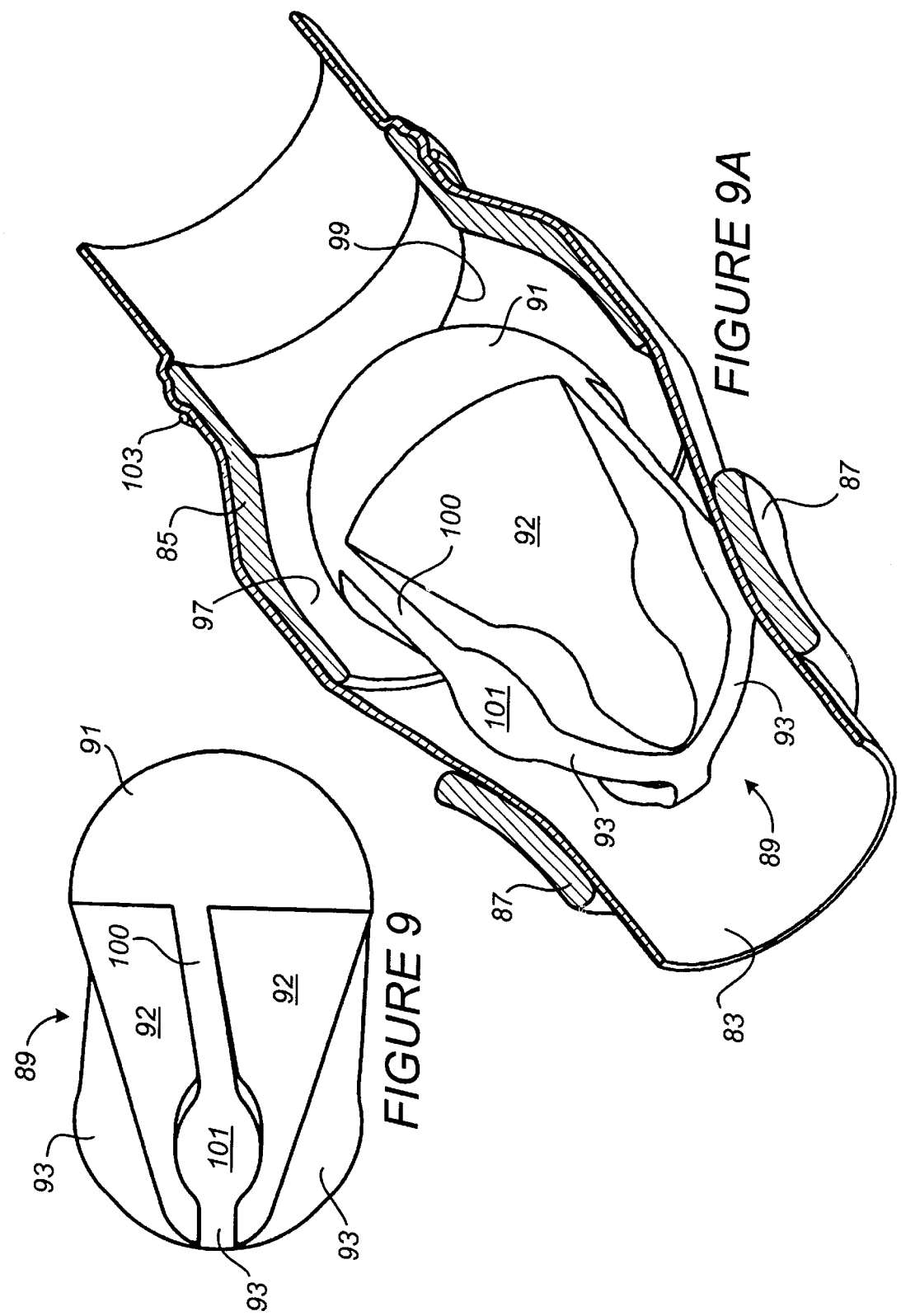
FIG. 9 is an elevational view of the occluder shown in FIG. 8 rotated 90° from the orientation therein.
Figure 10:
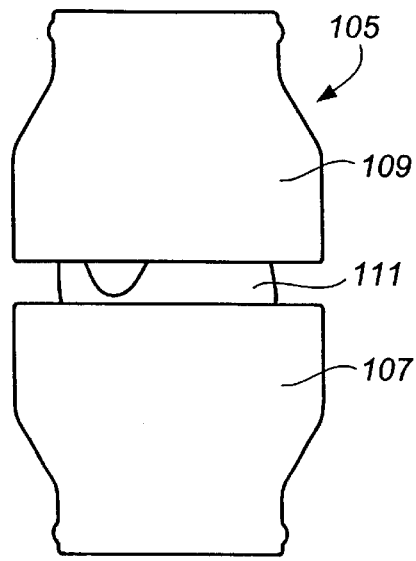
FIG. 10 is an elevational view of yet another prosthetic venous valve embodying various features of the invention.

The upstream housing section 85 has an entrance end 95 of reduced diameter and a central cylindrical section having an interior surface 97 of greater diameter than the hemi-spheroidal end 91 of the occluder 89. The transition surface between the larger diameter interior surface 97 and the reduced diameter entrance end 95 provides a seat 99 against which the hemi-spheroidal upstream end 91 of the occluder is in sealing contact when the valve is in the closed position, as shown in FIG. 8. The fins 93 may be straight and axially aligned; however, as best seen in FIG. 9, they are preferably curved, e.g. helically oriented, or otherwise oblique to the central axis. The fins 93 have base sections 100 which are of generally constant thickness in order to provide valleys 92 therebetween of relatively large dimension to serve as blood flow passageways, but at their upper ends, the fins are formed with enlarged pad sections 101 of wider dimension for a purpose explained hereinafter.

As previously indicated, the downstream section 87 of the housing is of split collar construction and is installed in surrounding relationship to the exterior of the vein. It may be of rigid material, such as a curved split sleeve of pyrocarbon, or it may be of a polymeric material, such as Gortex, that is shaped as desired. In either event, it may be directly sutured in place and/or wrapped about its exterior with gauze and then sutured in place. The collar may be located a desired distance downstream from the upstream section 85 of the valve after it has been secured in location using an appropriate tie 103 or the like, as previously maintained with respect to the valve 11.

In operation, when the patient is standing still, the valve 81 is in the position shown in FIG. 8 with the occluder 89 forced against the seat 99 in the upstream housing section of the valve, thus closing the valve and preventing blood from pooling up in the lower leg and generating excessive pressure. As the leg muscles are moved or tensed, a natural venous pump is activated which pumps toward the heart. The enlarged pad sections 101 near the downstream ends of the three fins 93 contact the interior surface of the vein and halt the occluder at this location, with the blood flowing through the valleys 92 between the three equally spaced-apart fins 93 as depicted in FIG. 9A. As previously indicated, the fins 93 are preferably obliquely oriented, as best seen in FIG. 9, or helically curved, so that the occluder 89 will have a tendency to rotate slightly about its axis each time it reciprocates between the open and closed position. As a result, the pad sections 101 near the ends of the fins 93 will not hit the exact same locations on the interior surface of the vein located within the upstream end region of the collar 87 each time it opens, but instead there will be essentially uniform contact with the vein surface about the 360° of this collar region over a multitude of valve openings. The materials for construction of the valve 81 may be the same as previously mentioned for the valve 11.

Figure 12:
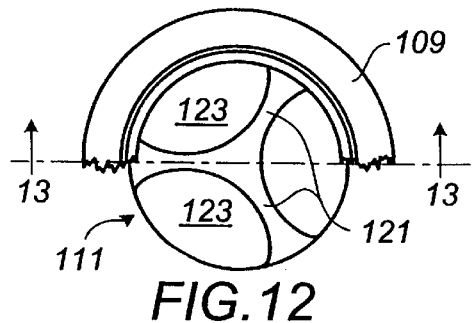
FIG. 12 is a fragmentary top view of the valve shown in FIG. 10.

Depicted in FIGS. 10–14 is another alternative embodiment of a venous valve 105 embodying various features of the invention which is slightly elongated in shape as compared to the valve 11. It includes an upstream housing section 107, a downstream housing section 109 and an occluder 111. The upstream housing section 107 has a construction similar to that of the housing section 13 being slightly more elongated in its central section 113 and formed with a similar seat 115. The downstream housing section 109 can be a duplicate of the upstream section 107 having a similar seat 117. The occluder 111 is elongated having the overall shape of a right circular cylinder with hemispherical ends from which three diagonal slices have been removed, positioned at 120° intervals. More specifically, the occluder has a hemispherical upstream end 119 that is sized to seal against the seat 115. The downstream end of the occluder 111 has a partial hemispherical surface in the form of three smooth ridges 121 (as best seen in FIG. 12). The three slices that are removed from the theoretical shape provide three planar surfaces 123 that create flow passageways or valleys between the three ridges 121.

Figure 13:
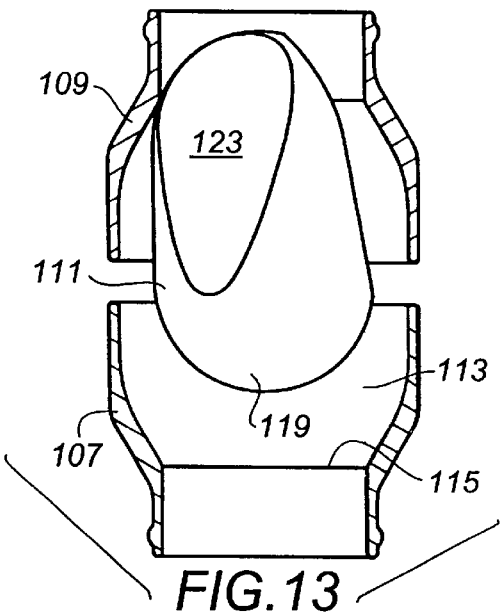
FIG. 13 is a sectional view taken generally along line 13—13 shown in FIG. 12 with the occluder shown in the open position and in elevation.
Figure 11:
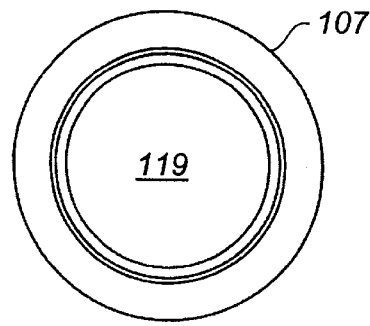
FIG. 11 is a bottom view of the valve shown in FIG. 10.
Figure 14:
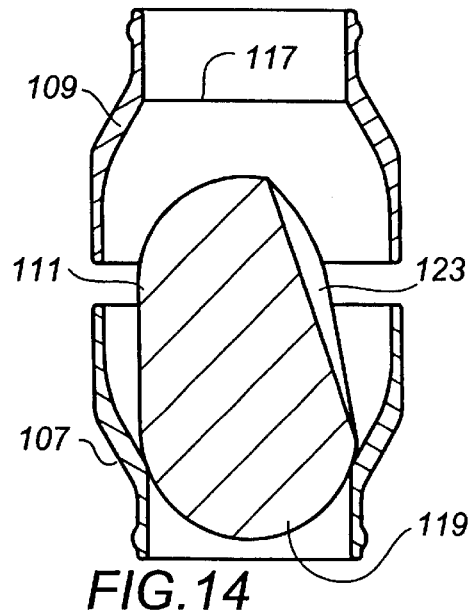
FIG. 14 is a view similar to FIG. 13 showing the occluder in section and in the closed position.

In response to pressure gradients, the elongated occluder 111 moves between a closed position illustrated in FIG. 14 where the hemispherical upstream end 119 is in sealing contact with the seat 115 and an open position illustrated in FIG. 13. In the open position, the three ridges 121 contact the seat 117 at approximate 120° intervals with the blood flowing downstream through the flow passageways provided by the flat surfaces 123.

Figure 15:
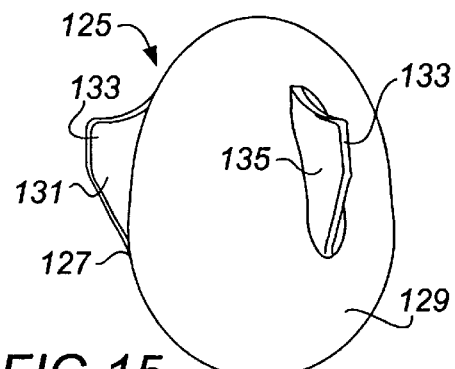
FIG. 15 is an elevational view of an occluder, enlarged in size, that might be alternatively used in the valve body of FIG. 10.

Illustrated in FIG. 15 is an alternative embodiment of an occluder 125 that might be used in a valve having a pair of upstream and downstream housing sections generally similar to the sections 107, 109 wherein the downstream section 109 is slightly elongated. The occluder 125 has a generally torpedo-shaped body 127 with a hemispherical upstream end 129, with the downstream portion of the body being generally ovoid. The occluder includes three fins 131 which extend radially outward from the ovoid body. The fins 131 have straight, radially outer, guide surfaces 133 with obliquely oriented flat or curved lateral surfaces 135, and they are arranged at equal intervals about the occluder. The straight surfaces 133 guide and slide against the interior surface of the downstream housing section 109 as the occluder 125 moves between its open and closed positions. The oblique orientation of the fins 131 causes the occluder to rotate about its axis.

Although the invention has been described with certain preferred embodiments, which include what is presently considered to be the best modes of carrying out the invention, it should be understood that various changes and modifications that would be obvious to one having the ordinary skill in this art may be made without departing from the scope of the invention which is defined by the claims appended hereto. For example, although some of the housing sections are shown as generally being secured within the vein by ties that are looped around the vein, it should be understood that other methods as known in this art, for example suturing, could be alternatively employed. Although three fins or detents are generally illustrated, more or less could alternatively be used in any of the valves illustrated. Although there are advantages in having the upstream and downstream sections of the housing spaced apart in its operative environment, it should be recognized that the facing ends of the housing sections could be easily shaped so as to interengage so as to create a continuous valve body in which the occluder would be confined. Instead of the wire cage 73, an alternative form of a surrounding retainer may be used, e.g. a perforated tube. The disclosures of all U.S. patents mentioned herein are expressly incorporated herein by reference.

Particular features of the invention are emphasized in the claims which follow.

What is claimed is:

1. A prosthetic venous valve which comprises
a generally tubular housing including an upstream section made of rigid material and a separate downstream section,
said upstream section comprising a rigid tubular body which provides a flow path for blood having an open entrance passageway and enclosing a first central region,
said downstream section comprising a rigid tubular body which provides a flow path for blood having an open discharge passageway and enclosing a second central region,
a separate occluder proportioned to move between said central regions,
said upstream section being formed with a seat in its interior surface in said first central region for sealing contact with said occluder to prevent blood flow upstream therepast and through said entrance region,
said occluder reciprocating between an open position adjacent said second central region and a closed position in contact with said seat in said first central region, and
said second central region of said downstream section having an inner surface formed to prevent the escape of said occluder downstream therethrough, said occluder and said inner surface being shaped so that when said occluder is in said open position a path remains open to said discharge passageway,
whereby this separate construction allows said upstream and downstream sections to be operatively implanted in a patient spaced apart from each other.

2. The venous valve according to claim 1 wherein each of said upstream and downstream sections carries, on the exterior surface thereof, means for positioning said sections at a desired spaced-apart location within a patient's vein whereby said sections and said occluder can be separately inserted through a longitudinally extending slit in a patient's vein and said separate sections individually secured in operable orientation in the desired location.

3. The venous valve according to claim 1 wherein said inner surface of said downstream section contains at least one detent extending generally radially inward from the remainder of said inner surface which prevents said occluder from moving therepast.

4. The venous valve according to claim 3 wherein said occluder is spheroidal in shape.

5. The venous valve according to claim 3 wherein said occluder is elongated in the direction of the axis along which said occluder reciprocates.

6. The venous valve according to claim 1 wherein said occluder is elongated in the axial direction along which it reciprocates and carries a plurality of radially outwardly extending fins which, in the open position, locate said occluder centrally with respect to said second central region by engagement with said rigid tubular downstream housing section in the open position and assure an open blood flow path downstream through said valve.

7. The venous valve according to claim 1 wherein a surrounding retainer is connected to exterior surfaces of said upstream and downstream sections and maintains said sections in desired spaced apart relation to each other with said occluder located therebetween.

8. The venous valve according to claim 7 wherein said occluder is a spheroid and wherein said upstream and downstream sections are spaced apart a distance equal to between about 40% and about 80% of the diameter of said spheroid.

9. The venous valve according to claim 7 wherein said surrounding retainer is a wire cage constructed of radioopaque wire material having sufficient stiffness to resist inadvertent bending and maintain said desired spacing in vivo within a patient.

10. The venous valve according to claim 7 wherein said surrounding retainer includes flexible barbs which in operative position extend diagonally outward from exterior surfaces of said upstream and downstream sections, but which can be resiliently positioned adjacent said exterior surfaces for installation.

11. The venous valve according to claim 10 wherein a plurality of said barbs are associated with said upstream section and extend diagonally in a downstream direction and wherein said barbs are associated with said downstream section and extend diagonally in an upstream direction.

12. A prosthetic venous valve which comprises
   a generally tubular housing including an upstream section made of rigid material and a separate downstream section,
   said upstream section having an open entrance passageway and a central region,
   said downstream section having a central region which is designed to face said central region of said upstream section and having an open discharge region of reduced diameter,
   a separate occluder proportioned to move back and forth between said central regions between an open position and a closed position when said valve is implanted within the vein of a patient,
   said upstream section being formed with a seat in its interior surface in said first central region surrounding said open entrance passageway for sealing contact with said occluder in said closed position to prevent blood flow upstream therepast,
   said discharge region of reduced diameter being of such size so as to prevent the downstream escape of said occluder therethrough, and
   said occluder being shaped so that, when it resides in said open position, a downstream blood flow path remains leading to and through said open discharge passageway, whereby said upstream and downstream housing sections can be separately implanted in a patient, spaced from each other in coaxial alignment, so they are capable of slight movement out of coaxial alignment independent of each other.

13. The venous valve according to claim 12 wherein said occluder is elongated and generally circular in cross-section, having an axial length at least about twice its diameter.

14. The venous valve according to claim 13 wherein said upstream end of said occluder is a portion of a spheroidal surface and said downstream end is formed with at least two equally spaced-apart fins.

15. The venous valve according to claim 14 wherein said upstream section and said occluder are designed for implantation within the vein of a patient and wherein said downstream housing section is designed as a collar for attachment exterior of the vein of the patient at a location appropriately downstream from said central region of said upstream housing section.

16. The venous valve according to claim 15 wherein said fins are of relatively uniform thickness except near their downstream ends where enlarged pads are provided for contact over an extended surface with the inner surface of the vein adjacent the upstream end of said collar-shaped housing section.

17. The venous valve according to claim 14 wherein said fins are obliquely oriented and thereby impart an axial rotation to said occluder when it reciprocates between said open position and said closed position.

18. A prosthetic venous valve which comprises
   a two-piece generally tubular housing including an upstream section made of rigid material proportioned for implantation within a patient's vein and a separate downstream collar section proportioned for implantation exterior of the patient's vein,
   said upstream section having an open entrance passageway and a first central region,
   said downstream section having an open discharge passageway and a second central region, and
   a separate occluder proportioned to move between said central regions,
   said upstream section being formed with an interior surface having a seat in said first central region for sealing contact with said occluder to prevent blood flow upstream therepast and through said entrance passageway,
   said occluder being designed to reciprocate between an open position in association with said second central region and a closed position in contact with said seat in said first central region, and
   said second central region of said downstream section having an inner surface formed to prevent the escape of said occluder downstream therepast, and
   said occluder and said inner surface being shaped so that when said occluder is in said open position a pathway remains open to said discharge passageway,
   whereby this two-piece construction allows said upstream and downstream sections to be separately operatively implanted in a patient.

19. The venous valve according to claim 18 wherein said occluder has a plurality of obliquely oriented fins which causes it to rotate about an axis as it reciprocates between said open and closed positions.

* * * * *